United States Patent [19]

Lee et al.

[11] Patent Number: 5,135,658
[45] Date of Patent: Aug. 4, 1992

[54] METHOD FOR REDUCING DETECTOR NOISE IN A CHROMATOGRAPHY SYSTEM

[75] Inventors: Kim W. Lee; Paul Feinstein, both of Berkeley; Randy Gordon-Gilmore, Benicia; Mark I. Fitchman, Woodland Hills, all of Calif.

[73] Assignee: Bio-Rad Laboratories, Inc., Hercules, Calif.

[21] Appl. No.: 520,533

[22] Filed: May 4, 1990

[51] Int. Cl.$^5$ .............................................. B01D 15/08
[52] U.S. Cl. .................................... 210/656; 210/101; 210/198.2
[58] Field of Search ...................... 210/198.2, 656, 101, 210/659; 73/61.1 C; 55/386; 366/132, 134, 152, 160, 182; 137/624.18

[56] References Cited

U.S. PATENT DOCUMENTS

| | | | |
|---|---|---|---|
| 3,446,057 | 5/1969 | Bakalyar | 210/198.2 |
| 4,427,298 | 1/1984 | Fahy et al. | 137/624.18 |
| 4,595,495 | 6/1986 | Yotam | 210/101 |
| 4,595,496 | 6/1986 | Carson | 210/198.2 |
| 4,767,279 | 8/1988 | Dourdeville et al. | 210/101 |
| 4,964,985 | 10/1990 | Goulder | 210/101 |

FOREIGN PATENT DOCUMENTS

| | | |
|---|---|---|
| 0105496 | 4/1984 | European Pat. Off. . |
| 61-035355 | 2/1986 | Japan . |
| 1-145483 | 9/1989 | Japan . |

OTHER PUBLICATIONS

Pharmacia Biotechnology Products Catalogue 85, 1985, pp. 1-51.

*Primary Examiner*—Robert A. Dawson
*Assistant Examiner*—Sun Uk Kim
*Attorney, Agent, or Firm*—Townsend and Townsend

[57] ABSTRACT

A controller (30) based chromatography system (2) especially designed for flexibility of operation with ease of use and an icon based control panel (32), has a number of function panels (34), each having a function key (36), one or more indicator indicia (40) in the form of icons, letters or numbers, and associated indicator lights (38). A switching valve (4) is used to provide a mixture of two or more solvents (6, 8) to a peristaltic pump (12). The cyclic nature of the pump and mixer can create a resonant condition resulting in poor quality information from the UV monitor (20). The system minimizes this by the judicious selection of the total cycle time T for the switching valve. This can be done using a random number manipulated in a manner to come up with each time T. Alternatively, an irrational number is combined with the pulsation frequency of the pump to create each time T. A valve driver circuit (170) used with a valve (172) of the type which requires a higher voltage switching signal (174) and lower voltage sustaining signal (176). The system permits the user to use three different nominal flow rate calibrations for peristaltic pumps using tubing having three different diameters (82, 84, 86). In addition to the precalibrated settings, the system can be user calibrated when desired.

5 Claims, 14 Drawing Sheets

METHOD FOR REDUCING DETECTOR NOISE IN A CHROMATOGRAPHY SYSTEM

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

It is often desired to separate mixtures of components into its constituents. One method, called liquidsolid chromatography, results in the separation of components of a sample in a liquid solvent through the movement of the solvent over a solid, typically housed within an enclosed pathway called a column. The sample is injected into the moving solvent before the solvent enters the column. The components of the sample travel at different rates through the solid depending on their affinities with the liquid/solid phases.

Liquid chromatography systems generally include a pump for pumping a solvent through the column. The liquid sample/solvent mixture exiting the column is often collected as a series of samples, called fractions, over a period of time by a fraction collector. Alternatively, or in addition, the constituents solvent/sample mixture from the column can be continuously monitored, such as through the use of an ultraviolet monitor.

One of the problems with conventional chromatography equipment is that it is generally assembled as a number of discrete components which are plumbed together according the particular requirements of the user. Control of the various chromatography system components has been through the use of computerized chromatography controllers which control various functions, such as solvent flow rate, valve operation, sample injection, gradient formation (that is, the mixture of two or more solvents at different proportions over time), and so forth. Although many of these controllers have been quite flexible, this flexibility has been at the expense of simplicity and ease of use.

What has been missing from the prior art is a liquid chromatography system which is designed to act in a coordinated manner emphasizing ease of use with simple, functional displays.

SUMMARY OF THE INVENTION

The present invention is directed to a coordinated chromatography system specially designed for flexibility of operation with ease of use and an icon based control panel.

The basic system includes a switching valve used to provide one or more solvents in predetermined portions to a pump. A dynamic mixer is used downstream of the switching valve along the solvent line to help achieve a uniform mix of the solvents from the switching valve. This is necessary because the switching valve alternatingly connects the solvents to the solvent line for periods of time determined by the proportions of the solvents. For example, if solvent A is to be 80% and solvent B 20%, the switching valve will connect solvent A to the solvent line 80% of the time and solvent B to the solvent line 20% of the time.

A sample injector valve is also positioned along the solvent line upstream on the column. A sample interrogation device, such as ultraviolet monitor, is positioned downstream of the column to monitor the composition of the solvent-sample mixture after it has passed through the column. A diverter valve is positioned downstream of the monitor to permit the liquid passing along the solvent line to be diverted as waste or to be directed to a fraction collector at the termination of the solvent line.

The switching valve, dynamic mixer, pump, sample injector, monitor, diverter valve and fraction collector are all generally conventional but are controlled by a novel controller. The controller includes an icon based control panel having a number of function panels. The function panels typically include a function key, one or more indicator lights and one or more indicator indicia. Where possible, the indicator indicia are visually meaningful icons. At other times the indicator indicia are alphabetical or numeric in form.

A calibration panel is used to calibrate the system with a particular inside diameter of the tubing is with the peristaltic pump. Several calibration indicator lights are used. One of the indicator lights is identified with indicator indicia represent calibration (typically "Cal" for calibrate). When the calibrate indicator illuminates, which is achieved by pressing the calibration key a number of times, the system is placed in a mode to permit the pump used with the system to be calibrated. The other indicator lights are used together with numeric indicator indicia representing the inside diameters of one or more standard sized tubes which can be used with a particular peristaltic pump. Illuminating one of the numeric indicator lights causes the system to use nominal calibration information for a standard size tubing designed for use with the system. Of course if nonstandard tubing is used, or if more precise calibration is needed, the manual calibration feature would need to be used.

Another aspect of the invention relates to a method for minimizing detector noise in the system. When the pump and the switching valve are both cyclic in nature, it is possible for their speeds to be such that mixing and flow of the solvents will not be uniform. This could create a resonant condition affecting the data from the monitor. There are at least two methods or systems which can be used to solve this problem. With both systems one must first choose the total cycle time period for the switching valve T to lie between minimum and maximum periods, for example, 2 to 4 or 5 seconds. The minimum and maximum periods are determined by the physical characteristics of the system, including the switching speed of the switching valve, the size of the dynamic mixer, and so forth.

In one system a random number is generated and then manipulated such that a "random" number time period between the minimum and maximum periods is created. The switching valve is then operated for that random number time period while splitting it between the solvents A and B according to the desired proportions. A new random number is generated and manipulated to create a new, random number time period for the next switching cycle. Even if a random number time period creates, or approaches, a resonant condition, the next random number time period will be different to minimize the resulting detector noise.

Another system for choosing a time period between minimum and maximum periods is accomplished by selecting an irrational number, such as the square root of 2, determining the pulsation frequency of the pump, combining the pulsation frequency and the irrational number to create an irrational frequency number. The irrational frequency number is multiplied by an integer to create a new time period, which is also an irrational number, between the minimum and maximum time periods. The switching valve is then operated for the new time period. Since the new time period is an irrational number, a resonant condition is not possible. The sequence is repeated using an updated new irrational frequency number (which depends upon the pump speed) for each time period of the switching valve.

A further aspect of the invention relates to a valve driver circuit used with a valve of the type requiring a switching voltage and a sustaining voltage, the switching voltage being in excess of the sustaining voltage. This achieved by using an R-C switch connected to the input signal line, the high supply voltage line and the first valve terminal. The R-C switch is configured to provide the switching voltage to the first valve terminal for a relatively short period of time when the input signal is first placed on the input signal line. The sustaining voltage is applied to the valve so long as the input signal is exerted on the input signal line. Doing so permits faster operation of the valve due to the higher supply voltage and the lower sustaining voltage. This is important when the valve is the switching valve by lowering the power consumed and the heat generated by the switching valve. Quick switching times also aid accurate proportioning between solvents.

A still further aspect of the invention relates to a drive circuit used when a stepper motor is used to drive the mixer. The drive circuit provides the mixer stepper motor with a ramped oscillating signal so that the stepper motor begins operating at a slower speed, gradually speeds up to the higher speed, drops down to the slower speed and repeats the cycle. This ramped frequency mixing cycle aids proper mixing of the solvents, especially ones with higher viscosities. For example, increasing the frequency of the drive signal to the stepper motor from 100 hertz to 250 hertz during a 10-second interval has proven effective.

Other features and advantages of the invention will appear from the following description, in which the preferred embodiment has been set forth in conjunction with the accompanying drawings.

DETAILED DESCRIPTION OF THE PREFERRED EMBODIMENT

The present invention is directed to a coordinated chromatography system 2 using an icon based control panel specially designed for flexibility of operation and ease of use.

Overview of System

Figure 1:
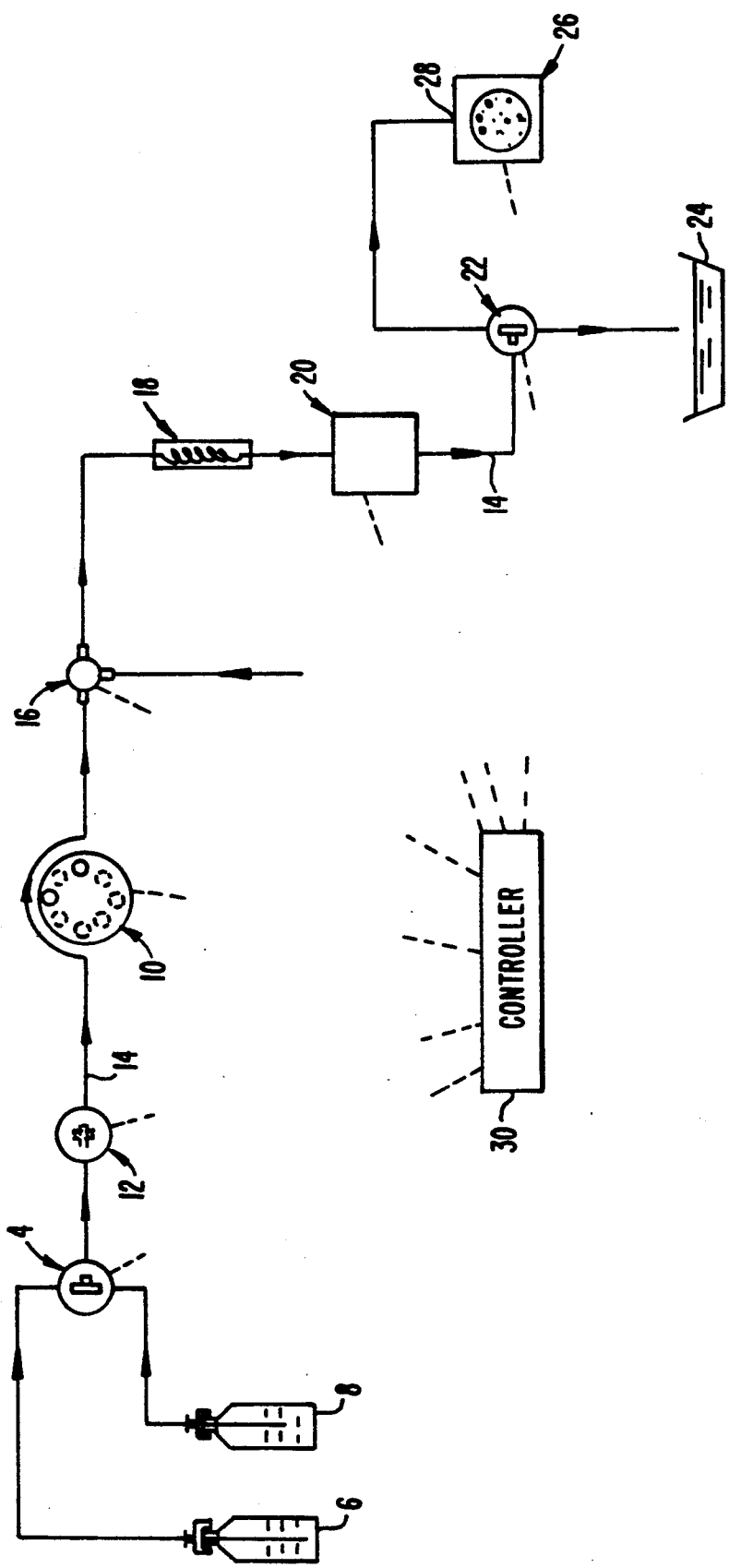
FIG. 1 is a schematic view of a liquid chromatography system made according to the invention.

System 2 is shown in FIG. 1 to include a switching valve 4 used to provide one or more solvents 6, 8 in predetermined portions to a pump 10. A dynamic mixer 12 is used downstream of the switching valve 4 along the solvent line 14 to help achieve a uniform mix of the solvents 6, 8 from the switching valve 4. This is necessary because the switching valve 4 alternatingly connects the solvents 6, 8 to the solvent line 14 for periods of time determined by the proportions of the solvents. For example, if solvent 6 is to be 80% and solvent 8 is to be 20%, the switching valve 4 will connect solvent 6 to the solvent line 14 80% of the time (e.g., 2.0 sec.) and solvent 8 to the solvent line 20% of the time (e.g., 0.5 sec.).

Pump 10, preferably a peristaltic pump, is positioned along the solvent line 14, in the preferred embodiment downstream of the mixer 12. Peristaltic pumps operate by rolling a number of rollers over a flexible tube to push the liquid through the tube. This type of pump is often used because the pump party are non-interactive with the solvents and the pump is relatively accurate. However, the cyclic nature of both the switching valve 4 and the pump 10 can create problems in monitoring downstream. System 2 has been designed to minimize the problems in a manner discussed below.

A sample injector valve 16 is also positioned along the solvent line 14 upstream of the column 18. A sample monitoring device, such as ultraviolet monitor 20, is positioned downstream of the column 18 to monitor the composition of the solvent-sample mixture after it has passed through the column. A diverter valve 22 is positioned downstream of the ultraviolet monitor 20 to permit the liquid passing along the solvent line to be diverted to waste 24 or to be directed to a fraction collector 26 at the termination 28 of the solvent line 14.

Figure 2:
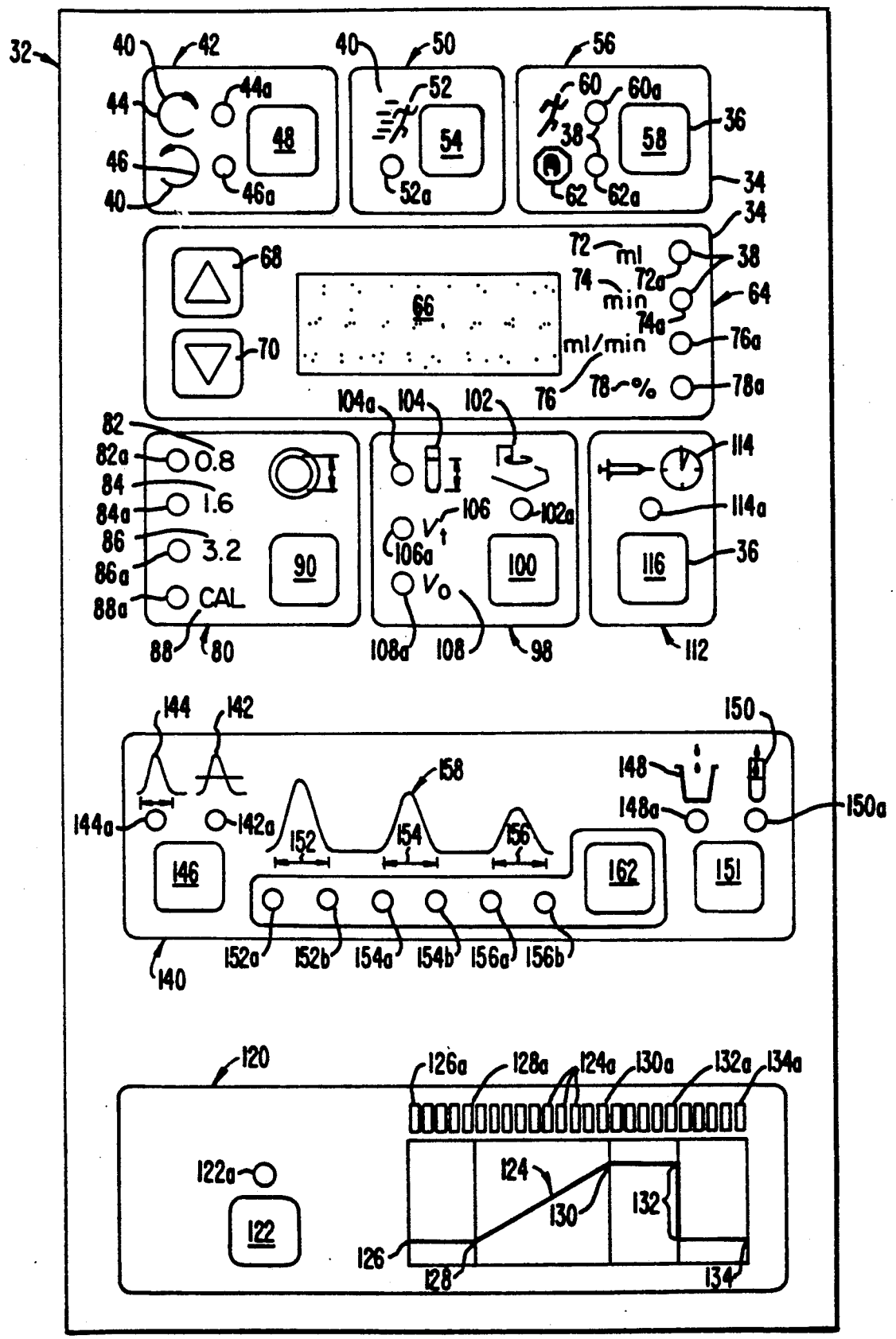
FIG. 2 is a front view of a control panel of the chromatography system of FIG. 1.

The switching valve 4, dynamic mixer 12, pump 10, sample injector 16, monitor 20, diverter valve 22 and fraction collector 26 may all be generally conventional and are all controlled by a controller 30. The controller 30 includes an icon based control panel 32, see FIG. 2, having a number of function panels 34. The function panels 34 typically include a function key 36, one or more indicator lights 38 and one or more indicator indicia 40. Where possible the indicator indicia 40 are visually meaningful icons; otherwise the indicator indicia are alphabetic or numeric in form.

The different function panels 34 of the preferred embodiment control panel 32 will now be described. A clockwise/counterclockwise panel 42 having a clockwise icon 44, a counterclockwise icon 46 and associated clockwise and counterclockwise indicator lights 44a, 46a. Pressing the clockwise/counterclockwise key 48 changes the direction of the pump 10 between clockwise and counterclockwise operation.

A purge panel 50 is used with a purge icon 52 and a purge indicator light 52a. The purge icon 52 is in the form of a running stick figure with speed lines indicating high speed. Pressing the purge key 54 actuates the pump 10 at its highest speed, that is 100% output. The purge key 54 is used to purge the system 2.

A run/stop panel 56 includes a run/stop key 58, a run icon 60, a run indicator light 60a, a stop icon 62 and a stop indicator light 62a. Pressing the run/stop key 58 turns the pump 10 on and off and illuminates the appropriate indicator light 60a, 62a.

A display panel 64 includes a multipurpose display 66 for alphanumeric information. The display panel 64 also includes arrow keys 68, 70 which are used to change various values, such as flow rate and sample size, shown on the display 66. Several indicator lights 38 are used with the display panel as well. The indicator indicia 40 for display panel 64 includes, preferably, abbreviations ml, min, ml/min and % as the volume indicium 72, the time indicium 74, the volume per unit time indicium 76 and the percent of full scale indicium 78 adjacent corresponding indicator lights 72a, 74a, 76a and 78a. Thus, when a particular indicator light is illuminated, this identifies the particular display value.

A calibration panel 80 is used to calibrate the flow through system 2. Tubing with different inside diameters can be used with the peristaltic pump 10. Several calibration indicia 82, 84, 86 and 88 are used on panel 80. With pump 10 stopped, pressing the calibration key 90 causes indicator lights 82a-88a to illuminate in succession. Controller 30 is programmed with three different standard calibration values for the particular pump 10 used with three commonly used tubing sizes. In the preferred embodiment, controller 30 is programmed for use with pump tubing having inside diameters of 0.8 mm, 1.6 mm and 3.2 mm corresponding to calibration indicia 82, 84 and 86. If the diameter tubing used with pump 10 corresponds to one of these three pre-programmed sizes, the user calibrates the flow rate by pressing key 90 until the appropriate indicator is illuminated. Pressing run/stop key 58 causes the system to operate with the chosen pre-programmed calibration.

At times the user may not know the size of tubing in the peristaltic pump 10, or may use a size tubing not listed, or may wish to have greater accuracy than that provided by the pre-programmed calibration values. In this case, with pump 10 stopped, calibration key 90 is pushed until indicator light 88a is illuminated. The run/stop key 58 is pressed and liquid is collected. Display 66 begins to time the calibration run, up to 5 minutes. When a suitable volume of liquid is obtained, run/stop key 58 is pressed again. Indicator light 72a begins flashing indicating the volume collected should be entered onto display 66 using keys 68, 70. Once the proper volume is entered, calibration key 90 is pressed again to confirm the calibration (a certain flow rate at a certain pump speed). Flow through system 2 can be started by pressing run/stop key 58. The flow rate shown on display 66 can be changed using keys 68, 70. To exit the calibration feature, press calibration key 90 once again so that all indicator lights 82a, 84a, 86a and 88a are off. If the pump speed is desired to be based upon percent of full speed operation, keys 68, 70 are used to choose the desired value.

The fraction collection panel 98 includes a fraction collection key 100, for fraction collection, indicator indicia 102, 104, 106 and 108 and associated indicator lights 102a, 104a, 106a and 108a. The indicator light 102a corresponding to the fraction collection enable icon 102 is illuminated when the fraction collector 28 is enabled. Pressing the fraction collection key 100 causes the display panel 64 to enter its edit mode with indicator light 72a flashing. The fraction volume icon 104 is a partially filled test tube. When the associated indicator light 104a is illuminated, the number shown on the display 66 represents the volume for a fraction to be collected. After the fraction volume is selected, key 100 is pressed again to illuminate indicator light 106a adjacent to the total volume indicium 106. The keys 68, 70 are again manipulated to select the total volume (Vt) to be collected as fractions by fraction collector 28. The process is repeated for the void volume (Vo) which is to be diverted to waste 24 at the beginning of the run by the diverter valve 22. Pressing key 100 once more illuminates the indicator light 102a for the fraction collection icon 102 signifying that the liquid passing through the solvent line 14 is being collected by the fraction collector 26.

The sample injection panel 112 includes a sample injection icon 114 having the representation of a syringe and a clock face. Pressing the sample injection key (also called the program run key) 116 while indicator light 114a is flashing starts the fraction collection program. If key 116 is pressed while the fraction collection program is being run, the program will be put on hold until key 116 is pressed again.

The gradient former panel 120 includes a gradient former key 122, an associated indicator light 122a, a gradient plot icon 124 (illustrating a typical gradient plot) and associated plots lights 124a. Pressing the gradient former key 122 once causes the percent indicator light 78a on the display panel 64 to flash along with the plot light 126a above the first gradient inflection point 126 on the gradient plot icon 124. The initial numeric display 66 reads zero, representing zero percent for solvent 8 and, thus, one hundred percent for solvent 6. Pressing the arrow key 68 and arrow key 70 on the display panel 64 allows the user to choose the desired percent for solvent 8 at the first gradient inflection point 126. When the appropriate value for solvent 8 is displayed, the gradient former key 122 is pressed again to confirm the entry. The lit gradient point lights 124a above the gradient plot icon 124, then advance to the second gradient inflection point 128. At this time, the time indicator light 74a on the display panel 66 is flashing. The desired time for the second point 128 is entered using the arrow keys 68, 70 and the time entry is confirmed by pressing the gradient former key 122. At this time, the flashing percent indicator light 78a on the display 64 signals the operator to enter the desired percent for solvent 8 at the second point 128. This again is accomplished by using the arrow keys 68, 70 on the display panel 64. When the desired value for percent of solvent 8 at the second point 128 is shown, the gradient former key is pressed again confirming the value. At this point, the plot light 130a above the third point 130 on the gradient plot icon 124 illuminates and the procedure is repeated for the third, fourth and fifth points 130, 132 and 134.

The system 2 can be operated at this point using the programmed gradients of solvents 6, 8. To do so, the run/stop key 58 is pressed, which causes the pump 10 to begin running at the initial gradient condition and the switching valve to begin mixing the solvents 6, 8 in the proportions indicated. To begin the programmed run, the program run key 116 is pressed. The display 66 will show the running time in minutes with the time indicator light 74a illuminated. To observe the other parameters of the program, the arrow keys 68, 70 are pressed to display the volume of output with the volume indicator light 72a illuminated, the flow rate with the flow rate indicator light 76a illuminated, or the percent of total running time passed with the percent indicator light 78a illuminated.

The peak collection panel 140 is used with a monitor, such as UV monitor 20, to allow the user to differentiate among various chromatographic peaks, using either a minimum threshold value or time windows. In the case of the minimum threshold, the fraction collector 26 begins collecting fractions so long as the value provided the controller 30 is above the minimum chosen through the peak collection panel 140. This is indicated by the minimum threshold icon 142 on the peak collection panel 140. Alternatively, the fraction collector 26 can be actuated to collect fractions during particular start and stop times, termed time windows, and indicated by a time window icon 144 on the peak collection panel 140. Collection by time windows is specially suited for situations in which it is known when particular peak values occur. The collector key 146 acts as a five-way switch with enter and confirm positions for both minimum threshold and time window collection methods, together with an off position. During periods in which the fraction collector 26 is not actively collecting factions, the liquid passing through the system passes through to waste 24 through diverter valve 22.

To collect fractions by threshold value, the collector key 146 is pressed until the indicator light 142a for the minimum threshold icon 142 is flashing. This causes the percent indicator light 78a on the display panel 64 to flash prompting the user to select the percentage of the full scale monitoring valve for monitor 20, typically absorbance. After selecting the minimum threshold value for absorbance (or other monitor value), the collector key 146 is pressed again to enable the threshold detection feature. The indicator light 142a below the minimum threshold icon 142 will be illuminated. To begin running the program using the minimum threshold collection criterion, the run/stop key 58 is pressed so that the indicator light 60a adjacent the run icon 60 is illuminated; the program run key 116 is the pressed. Note that the indicator light 148a corresponding to the waste icon 148 on the peak collection panel 140 is illuminated while the diverter valve 22 diverts the liquid flow to waste 24; the indicator light 150a corresponding to the fraction collect icon 150 is illuminated while the diverter valve 22 directs the liquid to the fraction collector 26. Diverter valve key 151 can be used to manually switch diverter valve 22 between waste 24 and faction collector 26.

Fraction collection by time windows is often used to collect fractions for materials known to elute at specific times during a run. In the preferred embodiment, the user can select three sets of starting and ending times corresponding to three time windows 152, 154, 156 as indicated beneath the peaks on the time collection icon 158. To select the time collection periods, the user presses the peak collector key 146 until the indicator 144a for the time window icon 144 begins flashing. The first indicator 152a of the six indicators beneath the time collection icon 158 is also illuminated. The time on the display 66 with the starting point for the first time window 152 is chosen using the arrow 68, 70. To confirm this value and illuminate the next indicator light 152b beneath the time collection icon 158, the time windows key 162 is pressed. The time for the end of the first time window 152 is entered on the display 66 using the arrow keys 68, 70. The process is repeated for a second and third time windows 154, 156. If only one time window is desired, the time windows key 162 is pressed until the last indicator 156b has been illuminated and turned off.

Figure 3A:
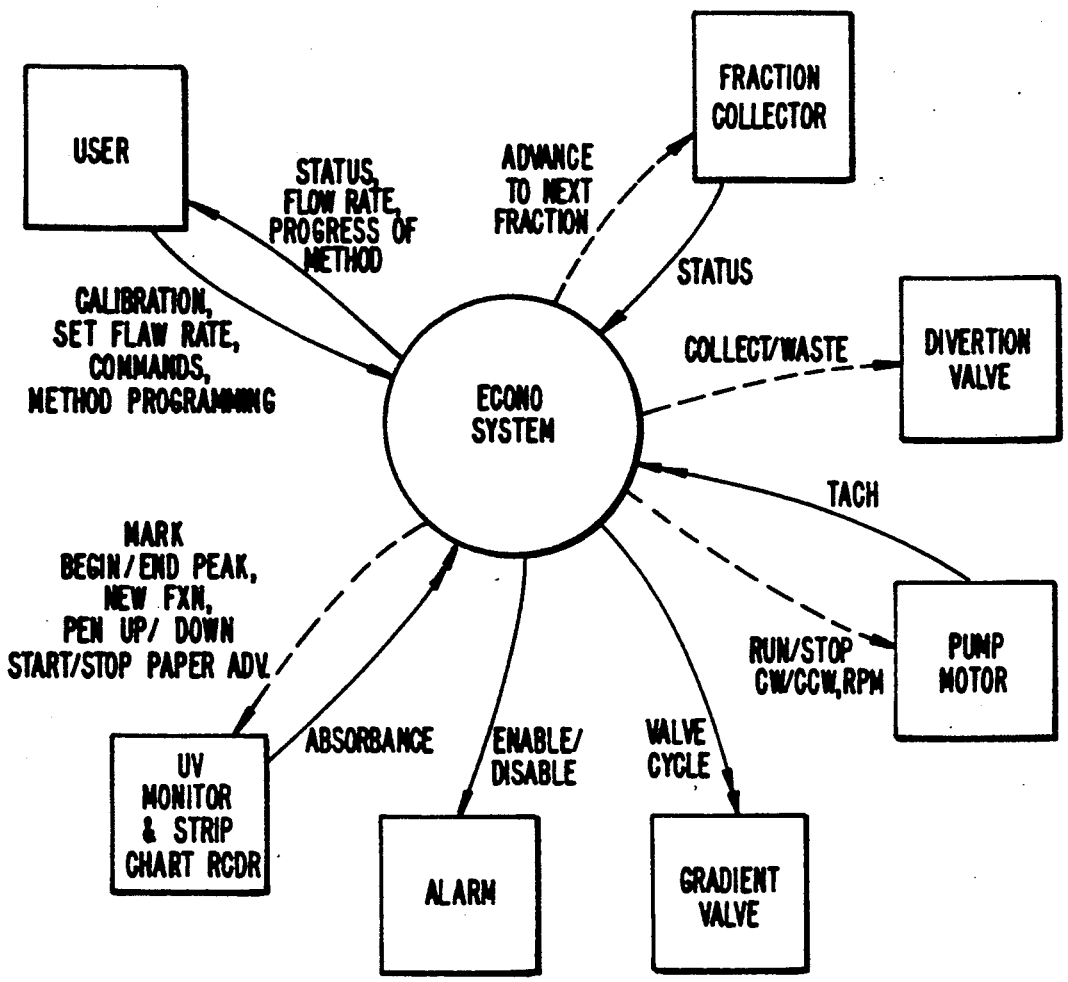
FIGS. 3A-3N are state diagrams and flow charts which describe the firmware used with the system of FIG. 1.
Figure 3N:
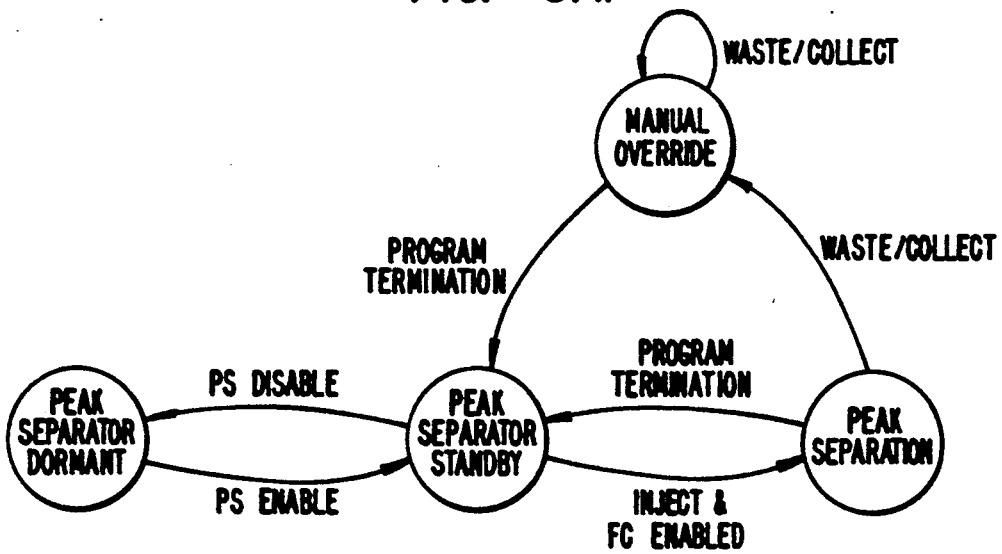
Figure 3B:
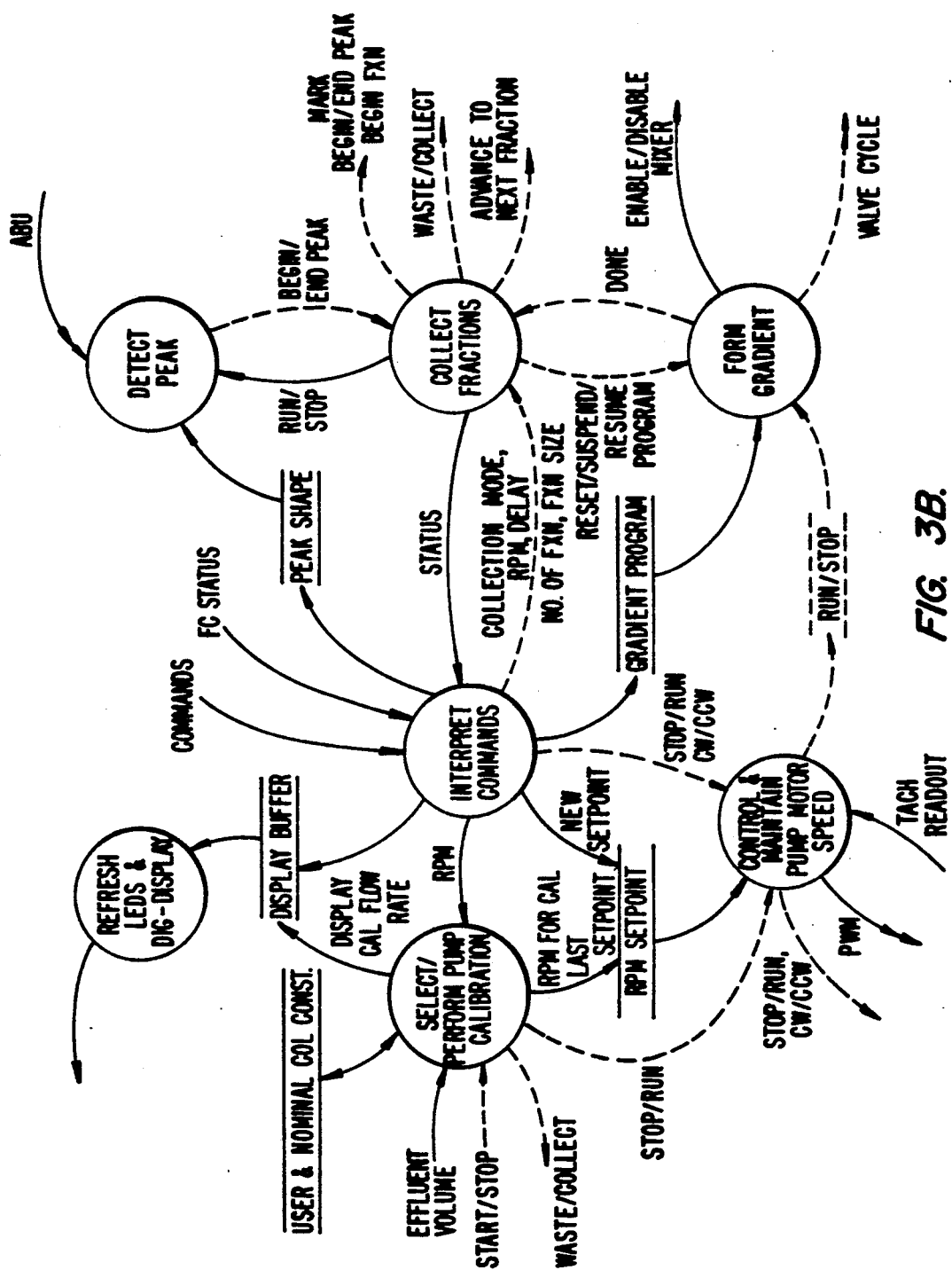
Figure 3C:
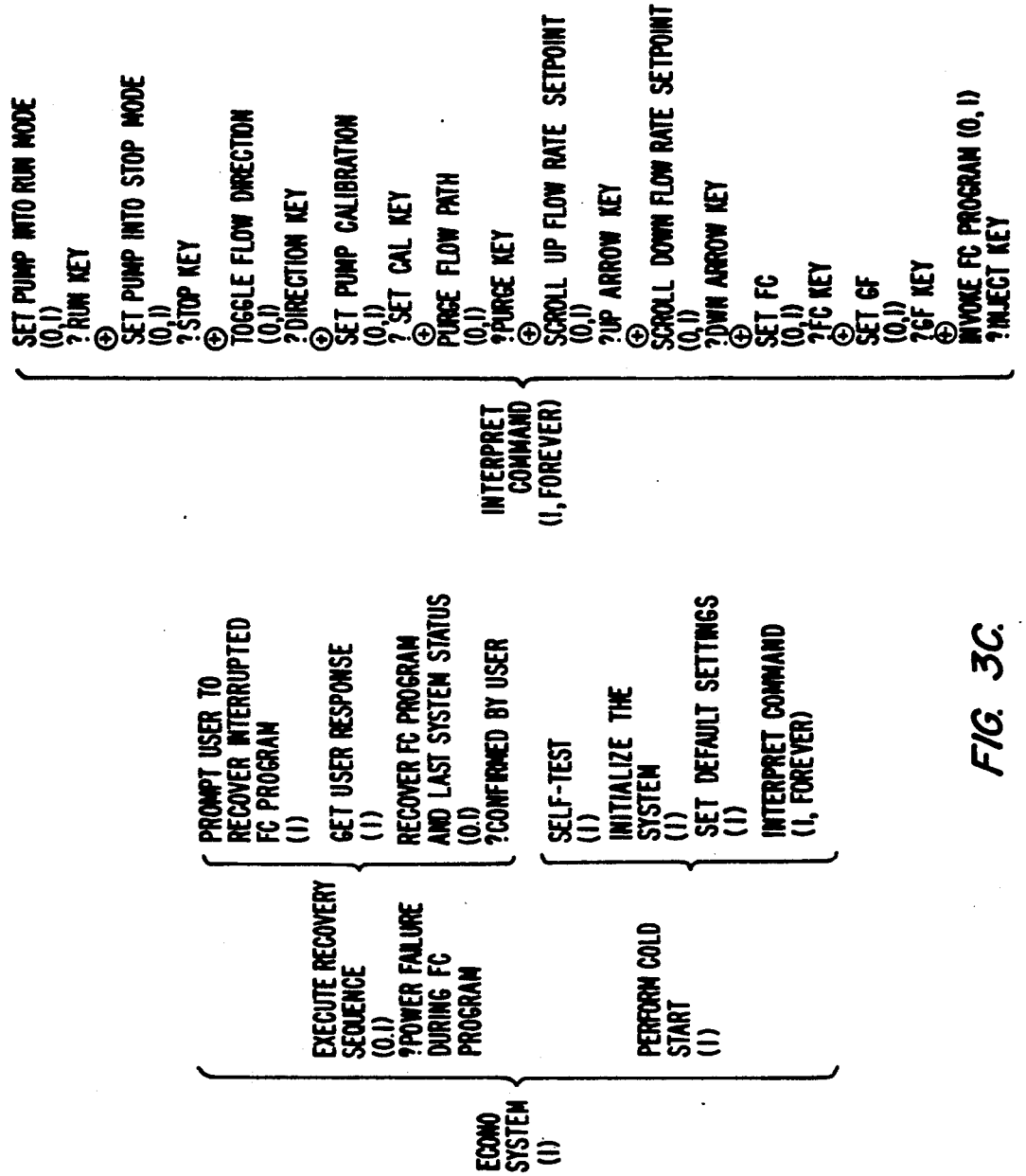
Figure 3D:
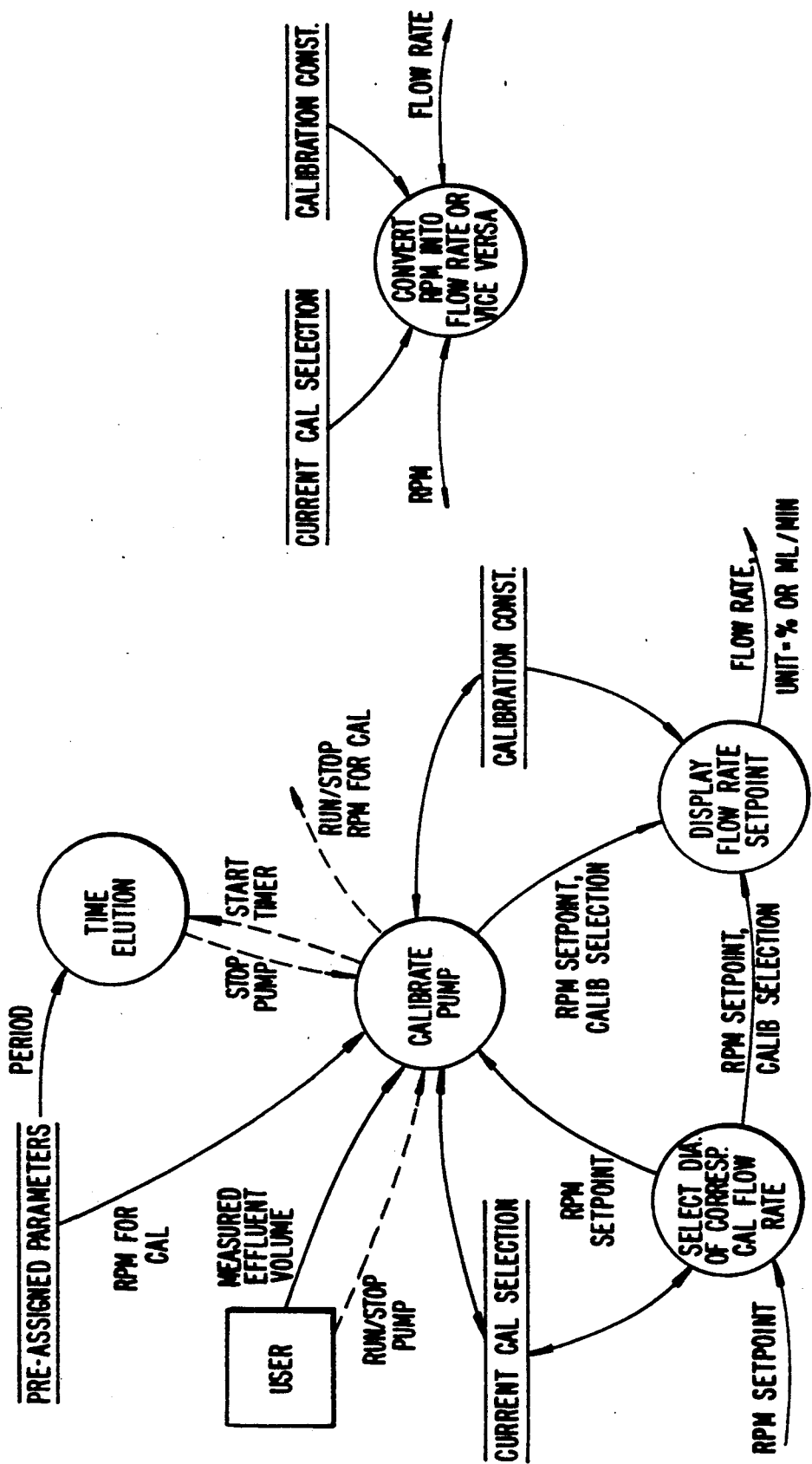
Figure 3E:
Figure 3F:
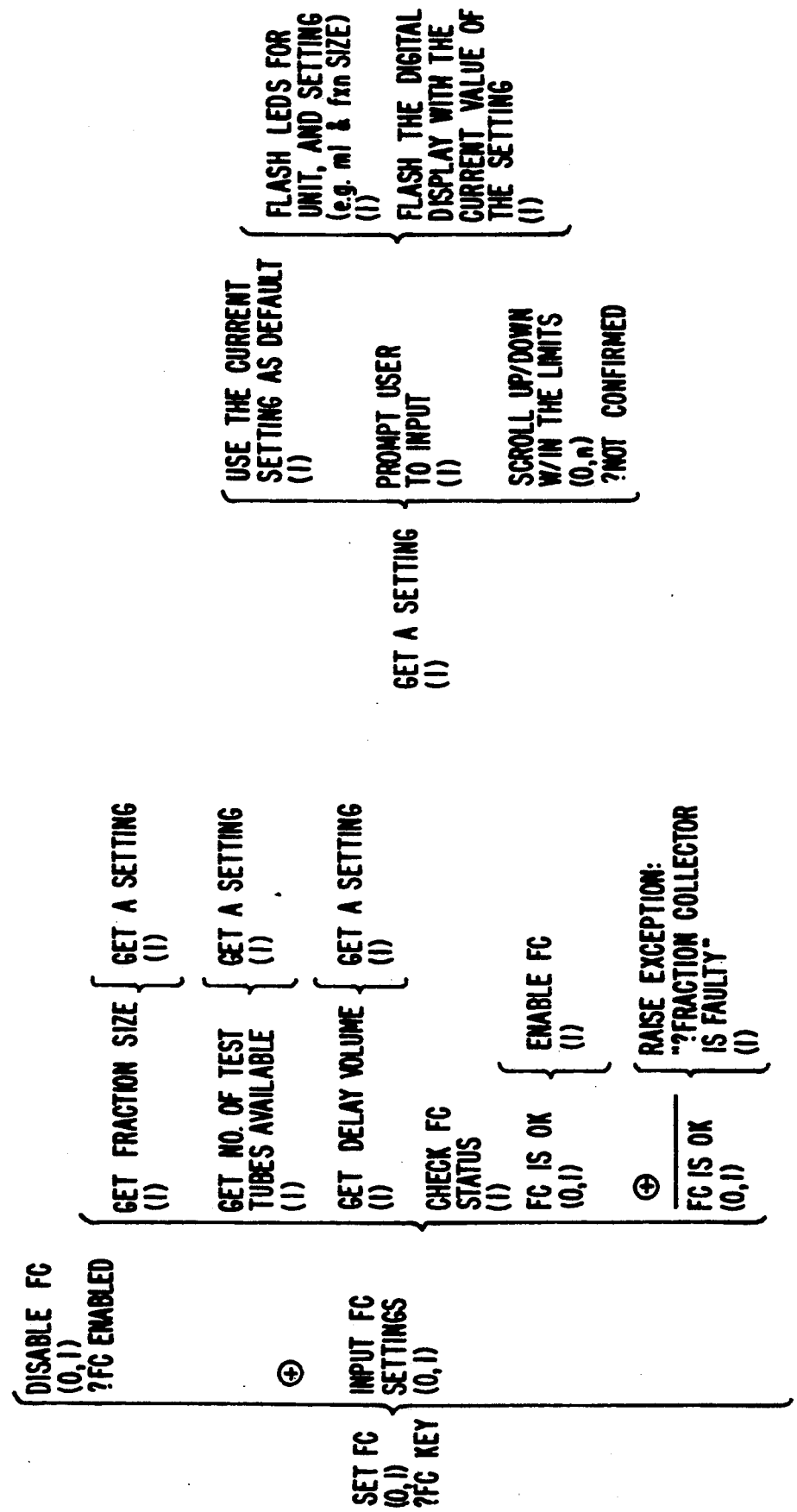
Figure 3G:
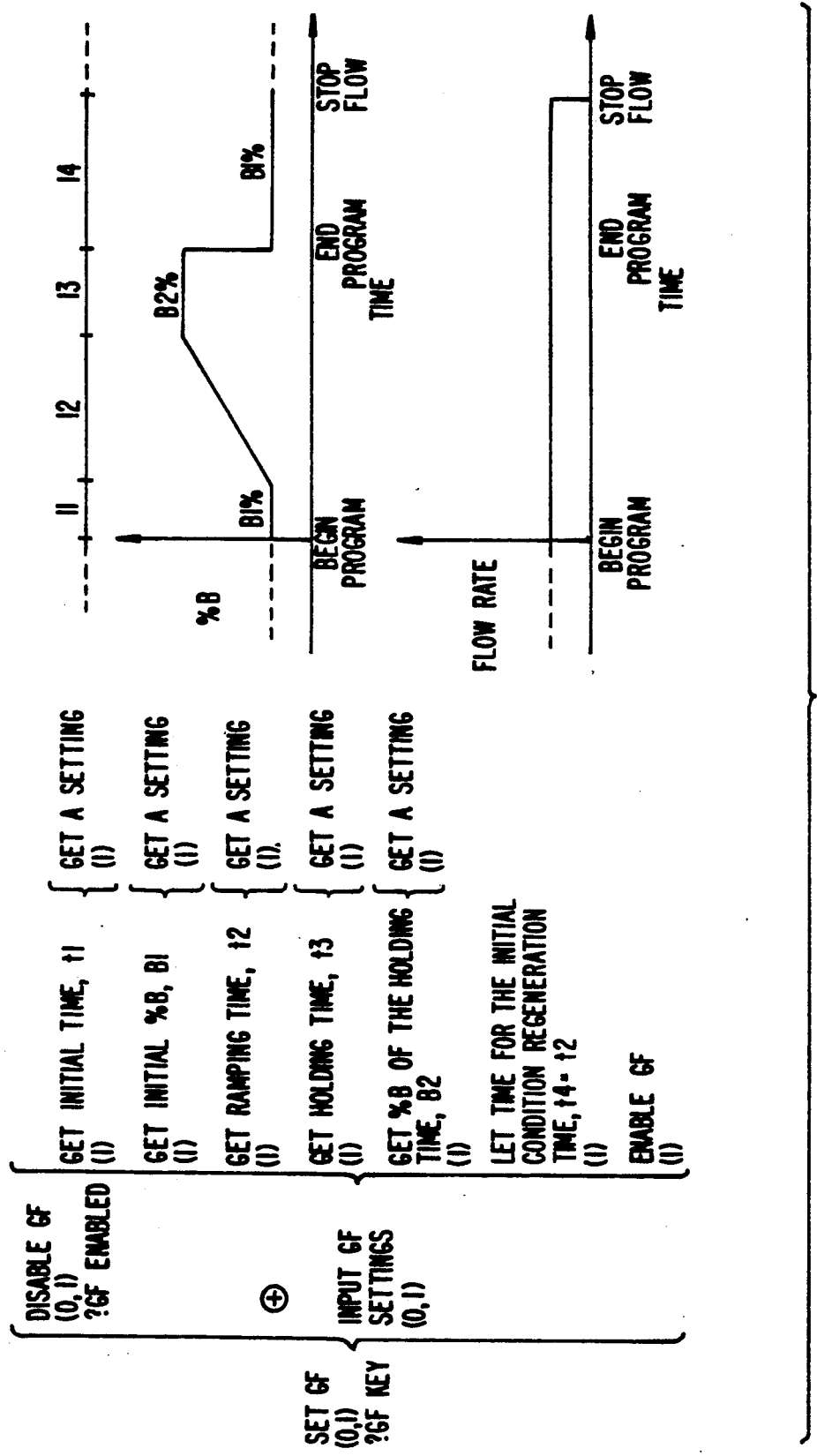
Figure 3H:
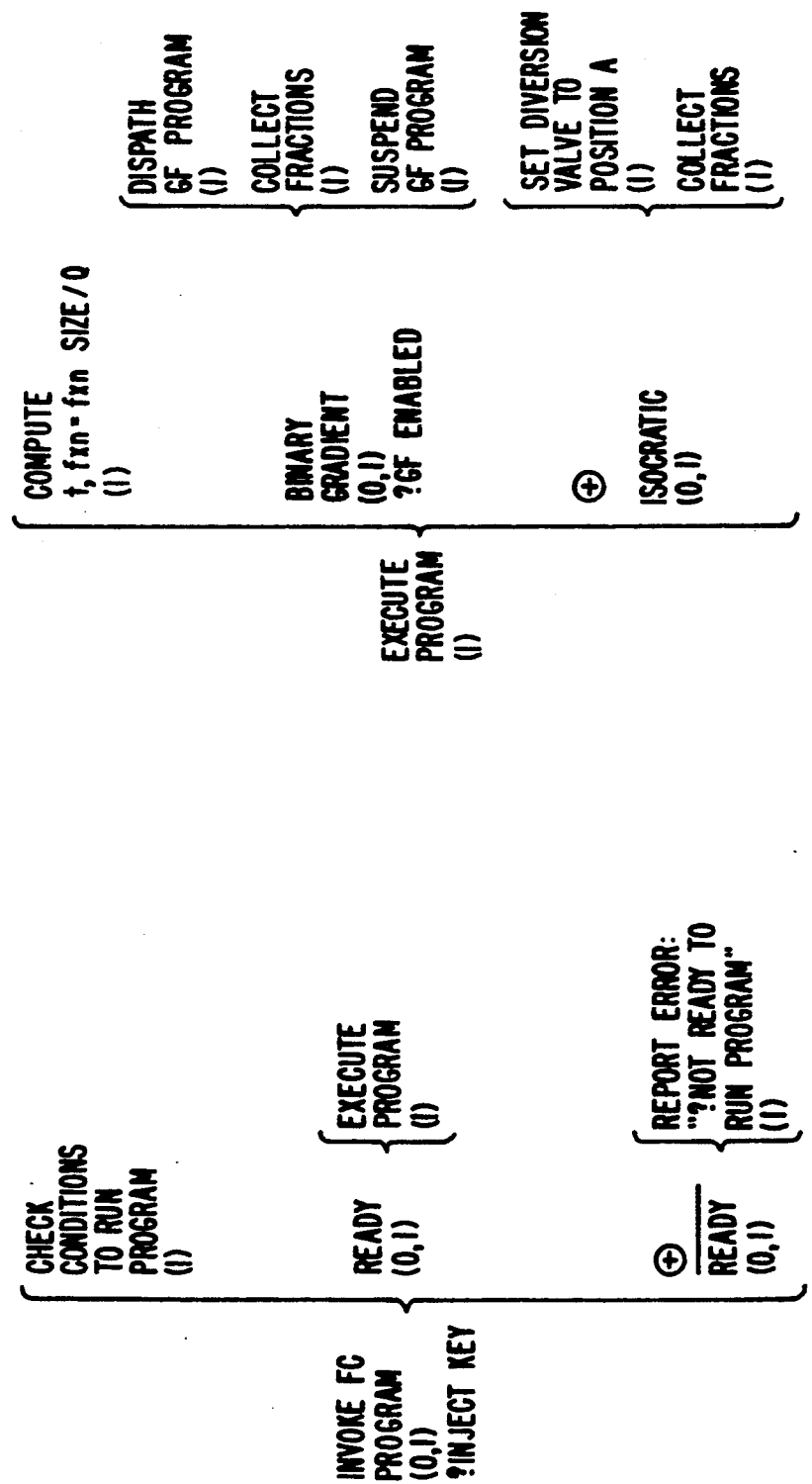
Figure 3I:
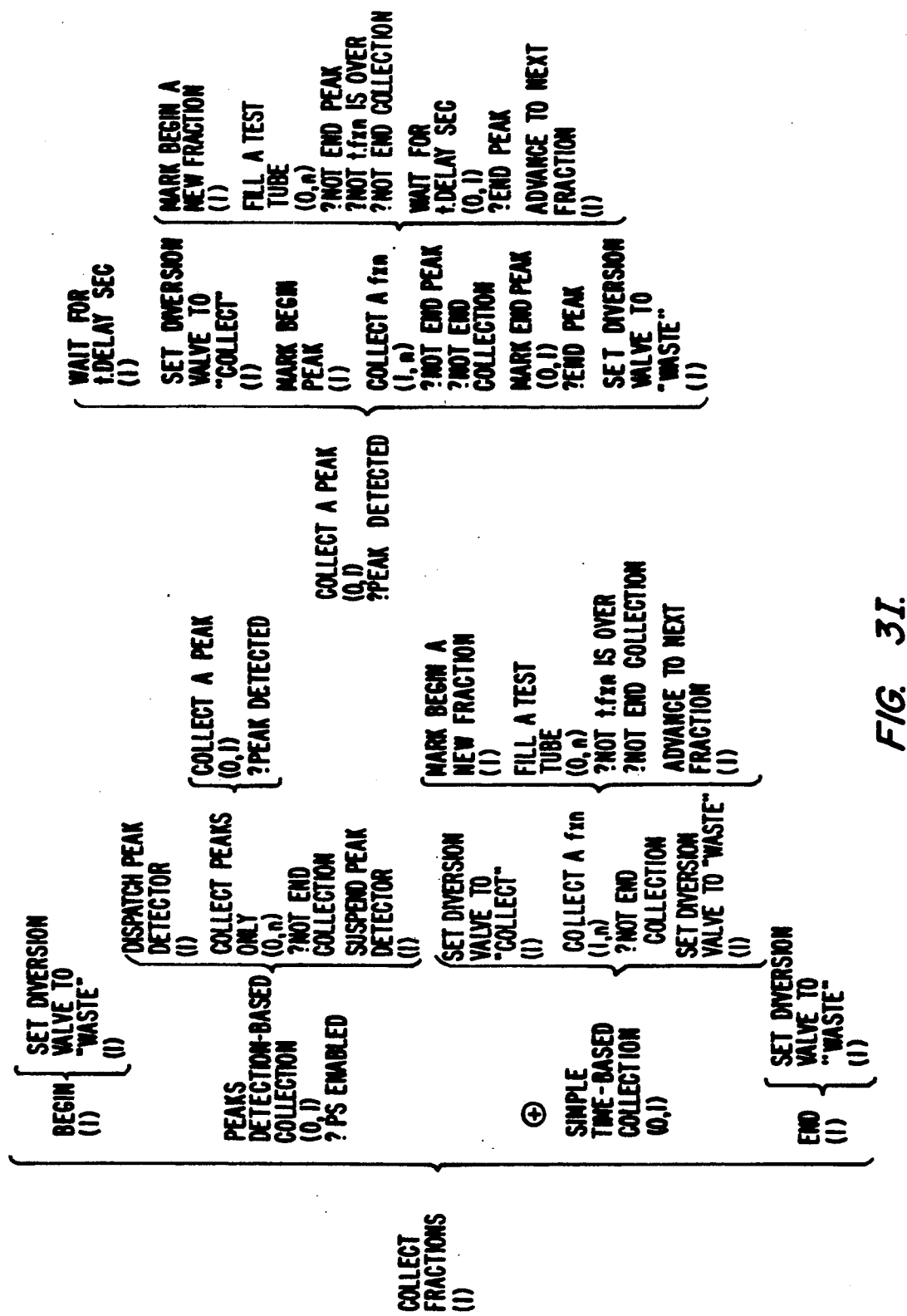
Figure 3J:
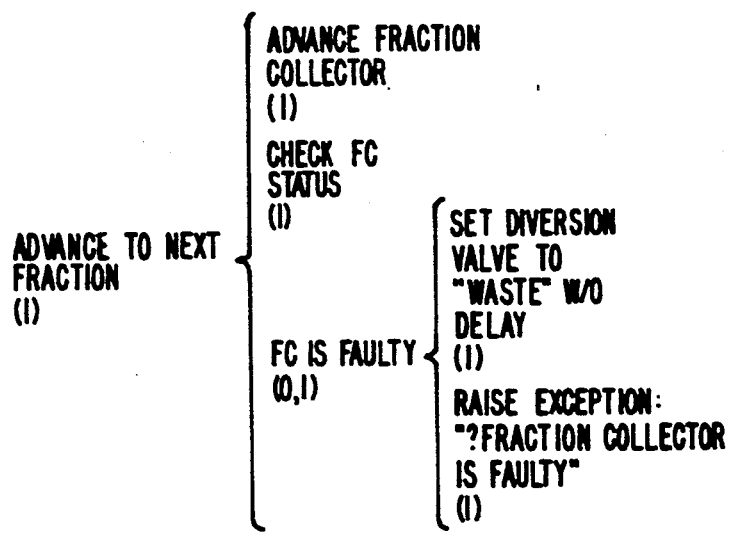
Figure 3K:
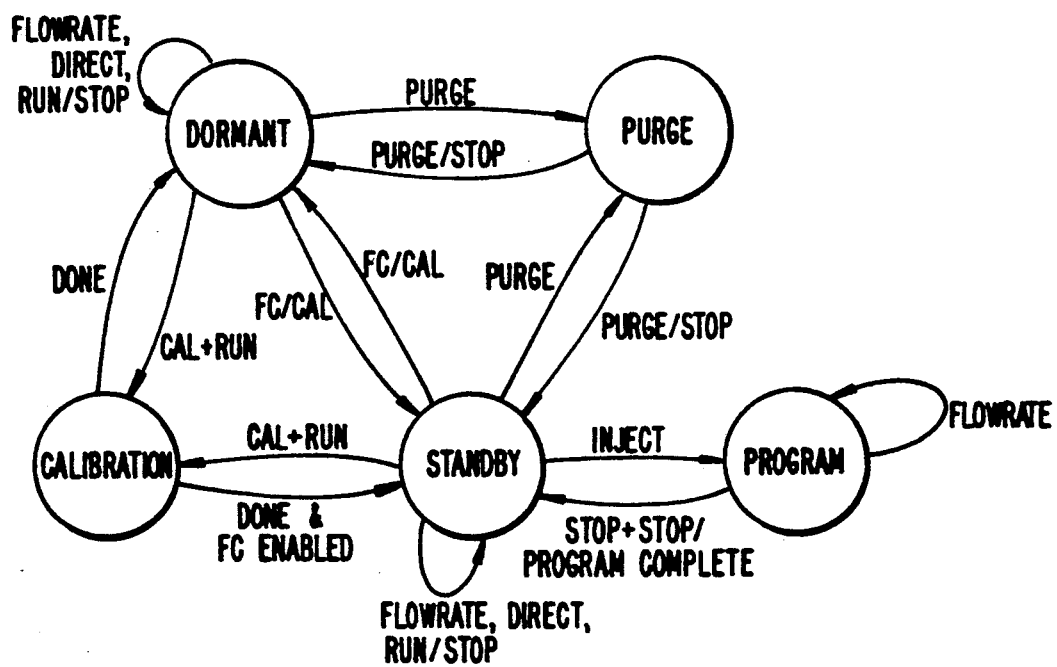
Figure 3L:
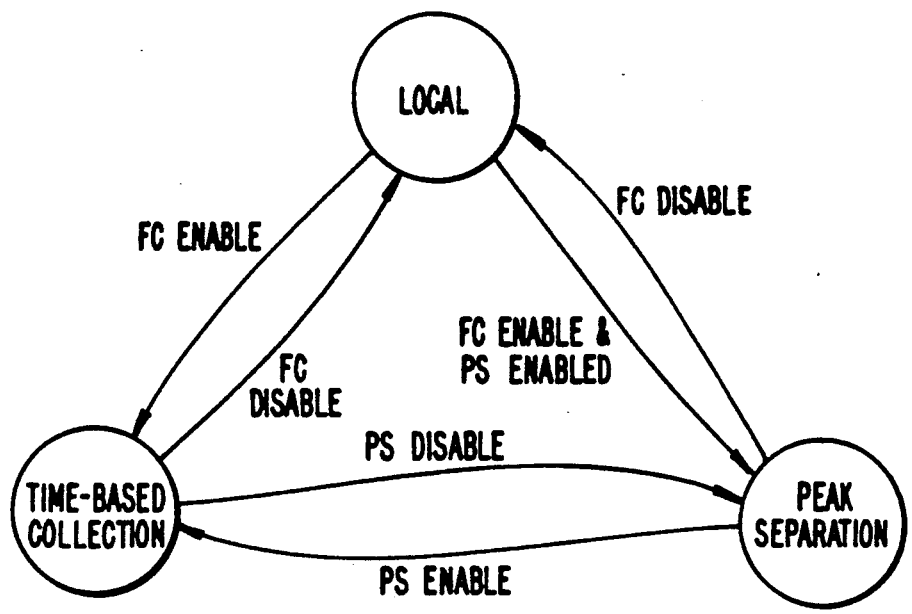
Figure 3M:
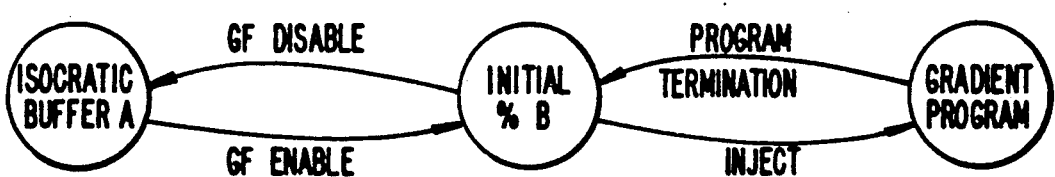

The above describes the system 2 in somewhat general terms. For further reference, please see FIGS. 3A through 3N which describes the firmware used with system 2 made according to a preferred embodiment.

Detector Noise Reduction

Another aspect of the invention relates to a method for minimizing detector noise in the system. Since the pump 10 and the switching valve 4 are both cyclic in nature, it is possible for their speeds to be such that mixing and flow of the solvents 6, 8 is not uniform. One way to solve this problem is by varying the period T during which the switching valve 4 cycles once between the two solvents 6, 8 while not creating a substantial risk of having the cycling of the switching valve coincide with the pump cycles. To do so, the total period T for each complete cycle of switching valve 4 is chosen to lie between minimum and maximum periods, in the preferred embodiment 2 to 4 seconds. The minimum and maximum periods are determined by the physical characteristics of the system 2, including the switching speed of the switching valve 4, the size of the dynamic mixer 12, and so forth.

One system for choosing T involves the generation of a random number and then manipulating the random number such that a "random" time period between the minimum and maximum times is created. The switching valve is then operated for the random time period while splitting it between the solvents 6, 8 according to the desired proportions at that point in time, taken from the gradient profile. A new random time period is generated from a new random number for the next switching cycle.

Specifically, system 2 determines the fraction B of solvent 8 from the gradient profile. A random number n is generated between 1 and 32,767. The length of the total time period T is calculated as $T=((n/32,767)*3)+2$. The portion $T(B)$ of T during which solvent 8 is passed through valve 4 is calculated as $T(B)=B*T$ and the portion $T(A)$ for solvent 6 calculated as $T(A)=T-T(B)$.

Another system for choosing T is accomplished by first selecting an irrational number, such as the square root of 2, determining the pulsation frequency of the pump 10 and combining the pulsation frequency and the irrational number to create an irrational frequency number. The irrational frequency number is multiplied by an integer to create a time period between the minimum and maximum time periods. The switching valve is then operated for the newly calculated time period. The sequence is repeated using a new irrational frequency number for each time period of the switching valve.

Preferably, the method proceeds as follows:

$P(new) = N*S(new)$ where:

$N$ = the number of rollers when the pump is a peristaltic pump;

$S(new)$ = the current rotational speed of the pump; and $P(new)$ = the number of pulses per second at $S(new)$.

$T(new) = (2**n)(2^{0.5})/P(new)$ where:

n is an integer such that T lies between 2 sec and 4 sec; and $T(new)$ is the total time period for that cycle of the switching valve 4.

Valve Driver Circuit

Figure 4A:
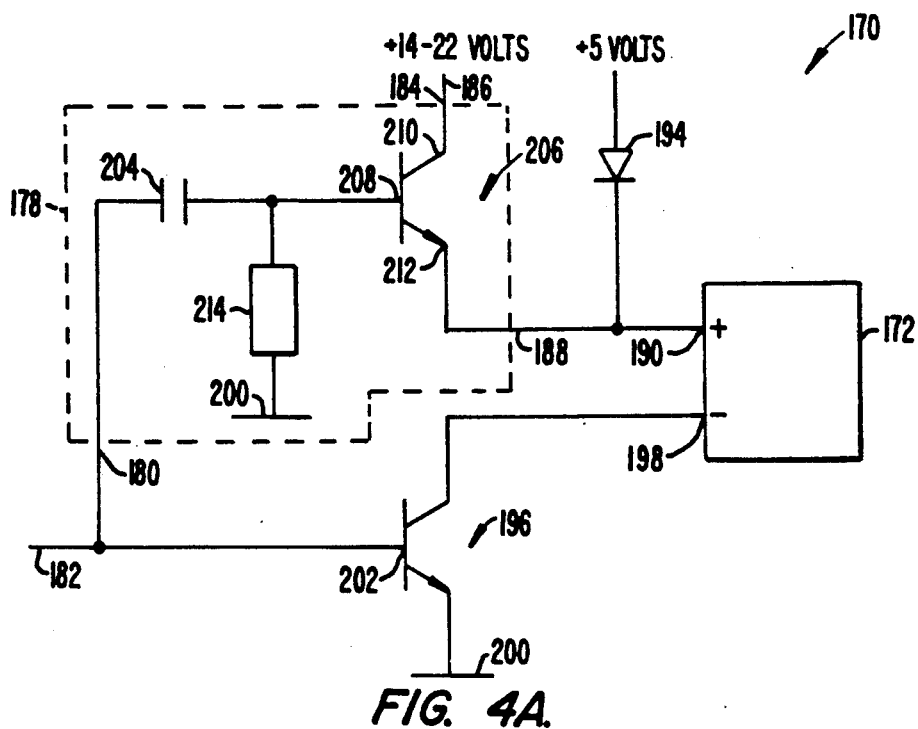
FIG. 4A is a schematic diagram of a valve driver
Figure 4B:
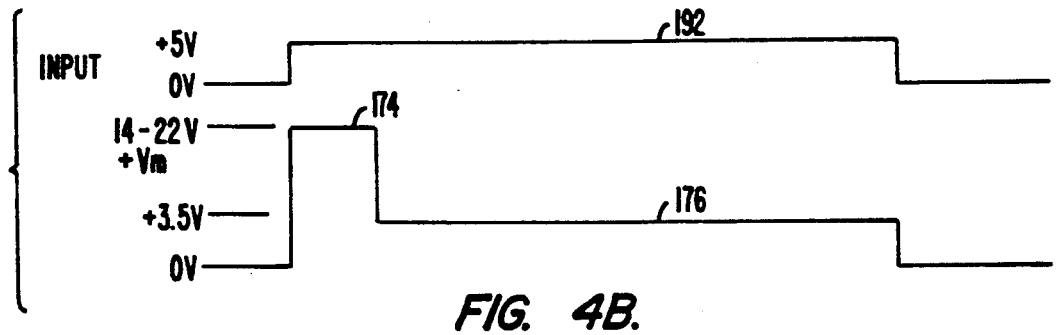
FIG. 4B is a voltage plot for the circuit of FIG. 4A.

A further aspect of the invention relates to a valve driver circuit 170 shown in FIGS. 4A and 4B. The circuit shown includes a valve 172 (such as diverter valve 22) requiring a switching voltage 174 and a sustaining voltage 176, the switching voltage being in excess of the sustaining voltage. This achieved by using an R-C switch 178 having a first terminal 180 connected to the input signal line 182, a second terminal 180 connected to a high (14-22 volts) supply voltage line 186 and a third terminal 188 connected to the first valve terminal 190. The R-C switch 178 is configured to provide the switching voltage 174 to the first valve terminal 190 for a relatively short period of time when the input signal 192 is first placed on the input signal line 182. The sustaining voltage 176 is applied to the first valve terminal 190 by the application of a lower, sustaining voltage (typically 5 volts) through a diode 194 (IN4007(CRx)) to the first valve terminal 190. A switching transistor 196 (actually an integrated circuit ULN2023A) couples the second valve terminal 198 to ground 200. The base 202 of the switching transistor 196 is connected to the input signal line 182. So long as the input signal 192 is exerted on the input signal line 182, and thus to the base 202 of the switching transistor 196, the switching transistor is on thus permitting current to flow through the valve 172.

R-C switch 178 includes a capacitor 204 (1μf) coupled to first terminal 180 and a transistor 206 (also an integrated circuit UDN2983A) having a base 208 connected to capacitor 204, a collector 210 connected to second terminal 184 and an emitter 212 connected to third terminal 188. R-C switch 178 also includes a resistor 214 (22k) coupling base 208 to ground 200.

During the initial period of time during the which the input signal 192 is applied to the input signal line 182, the R-C switch 178 is actuated thus permitting the higher voltage from the high supply voltage line 186 to be applied across the valve 172. After a relatively short period of time, e.g. 22 ms., chosen to be long enough to allow the valve to operate, the R-C switch 178 turns off so that a current passing through the valve 172 must come from the low or sustaining voltage source connected to diode 194. The voltage drops across diode 194 and transistor 196 create a voltage drop of about 3½ volts across the valve 172; this is high enough to keep the valve actuated but low enough to reduce the power consumption by the valve when in a sustaining mode.

Stepper Motor Drive Circuit

Figure 5A:
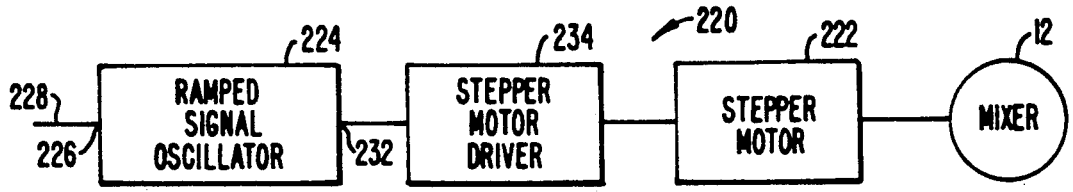
FIG. 5A is a schematic representation of the stepper motor drive circuit used with the system of FIG. 1.
Figure 5B:
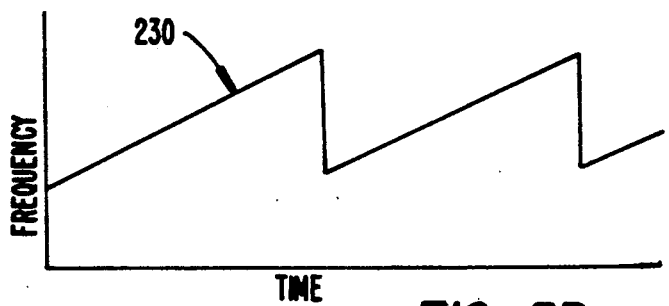
FIG. 5B is a frequency plot for the circuit of FIG. 5A.

A still further aspect of the invention relates to a drive circuit 220 used when a stepper motor 222 is used to drive the mixer 12. See FIGS. 5A and 5B. The drive circuit 220 includes a ramped signal oscillator 24 having an input 226 connected to the controller 30 by a signal line 228. Application of a drive signal to input 226 causes oscillator 224 to provide a ramped output signal 230 at its output 232. Signal 230 varies its frequency in a saw-toothed fashion as illustrated in FIG. 5B. Output 232 is connected to a stepper motor driver 234 which provides the mixer stepper motor 222 with a ramped frequency signal corresponding to the ramped output signal. This causes the stepper motor 222 to begin operating at a slower speed, gradually speed up to a higher speed, and then dropping back to the lower speed to repeat the cycle. Increasing the frequency of the drive signal to the stepper motor from 100 hertz to 250 hertz during a 10-second interval has proven effective. Varying the mixing speed improves the mixing effectiveness of mixer 12. The plot of signal 230 could be curved rather than straight and the lower speed could have zero, or even a negative number.

Other features and advantages of the invention will appear from the following description, in which the preferred embodiment has been set forth in conjunction with the accompanying drawings.

What is claimed is:

1. A method for reducing detector noise in a chromatography system of type including a switching valve, a cyclic pump, a column and a detector, the switching valve coupling first and second liquids to the pump for first and second time segment fractions X, Y out of a time period T according to the desired proportions of the first and second liquids, the method comprising:

choosing a range for T between a minimum time period T(min) and a maximum time period T(max);

selecting an irrational number IN;

determining the current pulsation frequency P(new) of the pump;

combining IN and P(new) to create a second irrational number IN(new) in a manner such that IN(new) is a number of time units;

multiplying IN(new) by an integer I(new) to create a time period T(new) between T(min) and T(max);

operating the switching valve using T(new) to connect the first liquid to the pump for a first time period equal to T(new) * X and to connect the second liquid to the pump for a second time period equal to T(new) * Y; and repeating the determining, combining, multiplying and operating steps while the pump is operating to pump a mixture of the first and second liquids through the system.

2. The method of claim 1 wherein the choosing step is carried out using T(min equal to 2 second and T(max) equal to 5 seconds.

3. The method of claim 1 wherein the selecting step is carried out by selecting the square root of 2 as IN.

4. The method of claim 1 wherein the determining step is carried out using the following formula when the pump is a peristalic pump:

$$P(new) = N * S(new)$$

where:

N = the number of rollers of the peristalic pump,

S(new) = the current rotational speed of the pump in revolutions per second; and P(new) = number of pulses per second at S(new).

5. The method of claim 1 wherein the operating step the first liquid is connected to the pump continuously during the first time period.

* * * * *